US009846145B2

(12) United States Patent
Yoshimura et al.

(10) Patent No.: US 9,846,145 B2
(45) Date of Patent: Dec. 19, 2017

(54) ULTRASOUND PROBE AND ULTRASOUND EQUIPMENT USING SAME

(71) Applicant: Hitachi, Ltd., Tokyo (JP)

(72) Inventors: Yasuhiro Yoshimura, Tokyo (JP); Tatsuya Nagata, Tokyo (JP); Akifumi Sako, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 234 days.

(21) Appl. No.: 14/377,265

(22) PCT Filed: Feb. 13, 2013

(86) PCT No.: PCT/JP2013/053335
§ 371 (c)(1),
(2) Date: Aug. 7, 2014

(87) PCT Pub. No.: WO2013/122075
PCT Pub. Date: Aug. 22, 2013

(65) Prior Publication Data
US 2015/0011890 A1    Jan. 8, 2015

(30) Foreign Application Priority Data

Feb. 14, 2012   (JP) ................................ 2012-029259

(51) Int. Cl.
*A61B 8/14*      (2006.01)
*G01N 29/24*     (2006.01)
(Continued)

(52) U.S. Cl.
CPC ........... *G01N 29/2406* (2013.01); *A61B 8/14* (2013.01); *A61B 8/4444* (2013.01);
(Continued)

(58) Field of Classification Search
CPC ....... A61B 8/44; A61B 8/4483; A61B 8/4494; A61B 8/4444; G01N 29/22; G01N 29/24; G01N 29/2406
See application file for complete search history.

(56) References Cited

U.S. PATENT DOCUMENTS

2007/0057603 A1   3/2007  Azuma et al.
2007/0180916 A1   8/2007  Tian et al.
(Continued)

FOREIGN PATENT DOCUMENTS

CN        1929699 A       3/2007
CN      101018428 A       8/2007
(Continued)

OTHER PUBLICATIONS

Extended European Search Report received in corresponding European Application No. 13748547.0 dated Oct. 2, 2015.
(Continued)

*Primary Examiner* — Tse Chen
*Assistant Examiner* — Jason Ip
(74) *Attorney, Agent, or Firm* — Mattingly & Malur, PC

(57) ABSTRACT

Provided are: an ultrasound probe with excellent characteristic stability; and ultrasound equipment that uses the ultrasound probe. The ultrasound probe has an ultrasonic transmitting and receiving element provided with a substrate, an insulating film formed on the substrate, a cavity formed between the substrate and the insulating film, and a pair of electrodes disposed parallel to the substrate so as to sandwich the cavity. The ultrasound probe is characterized in that the ultrasonic transmitting and receiving element has a beam part with a multilayer structure formed by laminating films made of materials different in stress, the beam part being disposed on the electrode distant from the substrate out of the pair of electrodes, and the beam part is formed by
(Continued)

laminating a film that applies tensile stress and a film that applies compressive stress.

10 Claims, 9 Drawing Sheets

(51) Int. Cl.
*A61B 8/00* (2006.01)
*B06B 1/02* (2006.01)

(52) U.S. Cl.
CPC ............ *A61B 8/4494* (2013.01); *A61B 8/461* (2013.01); *B06B 1/0292* (2013.01); *G01N 2291/028* (2013.01); *G01N 2291/044* (2013.01); *G01N 2291/101* (2013.01)

(56) References Cited

U.S. PATENT DOCUMENTS

| | | |
|---|---|---|
| 2007/0222338 A1 | 9/2007 | Aono et al. |
| 2007/0284682 A1 | 12/2007 | Laming et al. |
| 2008/0284287 A1 | 11/2008 | Yoshimura et al. |
| 2009/0301200 A1 | 12/2009 | Tanaka et al. |
| 2009/0322181 A1* | 12/2009 | Machida ............... B06B 1/0292 310/300 |
| 2010/0249605 A1 | 9/2010 | Degertekin |
| 2011/0151608 A1 | 6/2011 | Lemmerhirt et al. |

FOREIGN PATENT DOCUMENTS

| | | |
|---|---|---|
| CN | 101238754 A | 8/2008 |
| CN | 101385392 A | 3/2009 |
| EP | 1837087 A2 | 9/2007 |
| EP | 2002900 A2 | 12/2008 |
| EP | 2 145 696 A1 | 1/2010 |
| JP | 2005-252056 A | 9/2005 |
| JP | 2007-259165 A | 10/2007 |
| JP | 2008-283618 A | 11/2008 |
| JP | 2011-259186 A | 12/2011 |
| WO | 2007/046180 A1 | 4/2007 |

OTHER PUBLICATIONS

Chinese Office Action received in corresponding Chinese Application No. 201380008619.0 dated Jul. 8, 2015.

* cited by examiner

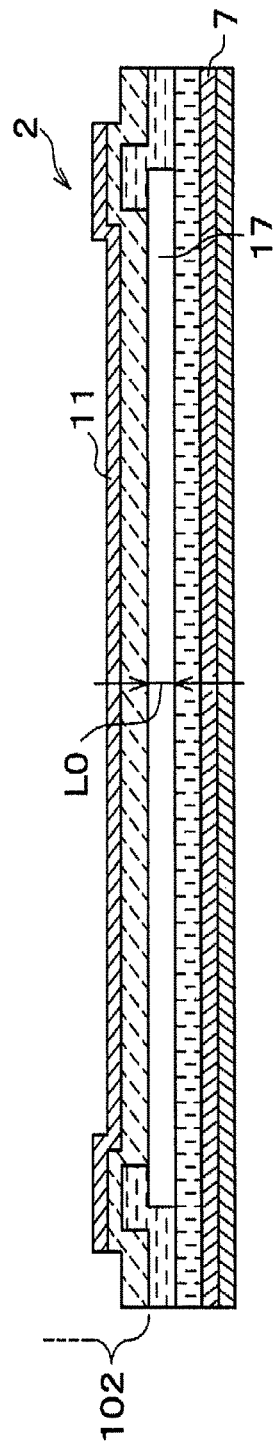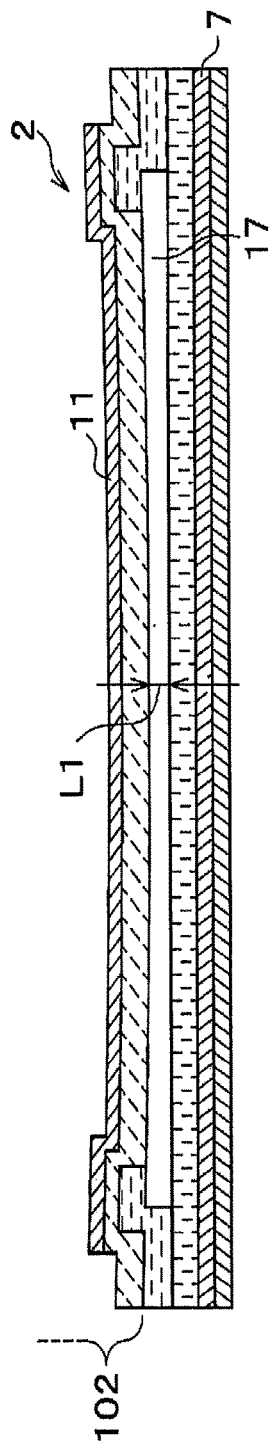

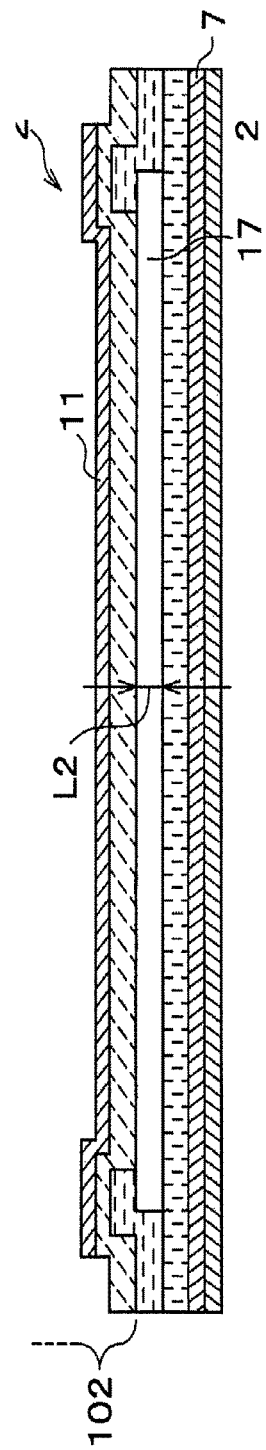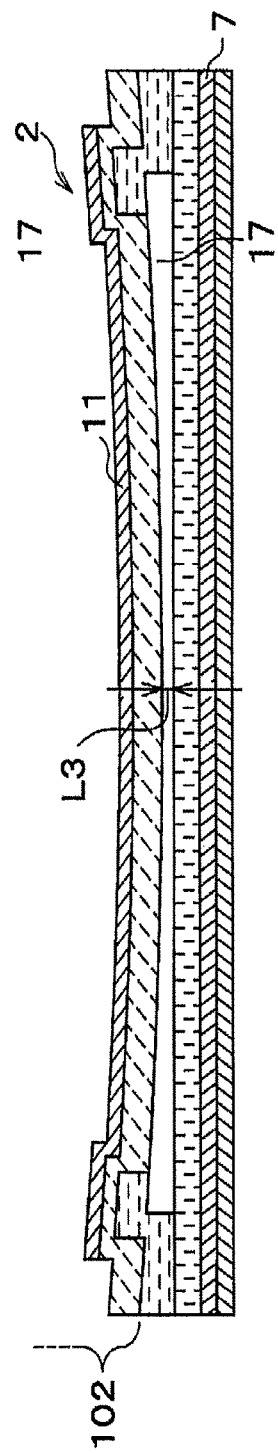

ULTRASOUND PROBE AND ULTRASOUND EQUIPMENT USING SAME

TECHNICAL FIELD

The present invention relates to an ultrasound probe and ultrasound equipment using the same.

BACKGROUND ART

An ultrasound probe is preferably used for ultrasound examination on a subject such as a human or an animal. As a technique related to such an ultrasound probe, there is one described in Patent Document 1, for example. To be more specific, with application of a semiconductor manufacturing technique and an MEMS (Micro Electro Mechanical System) technique, this technique is to manufacture an ultrasonic transmitting and receiving device by lamination of thin films. The ultrasonic transmitting and receiving device includes a lower electrode provided on a silicon substrate, an upper electrode provided above the lower electrode, and first and second insulating films provided above the upper electrode. The first and second insulating films are formed to apply tensile stress and compressive stress in combination to adjust warpage of a gap between the upper and lower electrodes.

Also, Patent Document 2 describes an ultrasonic transducer in which a substrate having a first electrode inside or on a surface thereof and a diaphragm having a second electrode inside or on a surface thereof are disposed with a cavity interposed therebetween, the ultrasonic transducer including at least one beam.

PRIOR ART DOCUMENT

Patent Document

Patent Document 1: Japanese Patent Application Publication No. 2007-259165
Patent Document 2: International Patent Application Publication No. 2007/046180 pamphlet

SUMMARY OF THE INVENTION

Problem to be Solved by the Invention

As described in Patent Document 1, a cMUT (Capacitive Micromachined Ultrasonic Transducer) element is an applied technique of the semiconductor manufacturing technique and the MEMS technique. To be more specific, since the cMUT element is manufactured by laminating films, a membrane (including multiple laminated films) that is a drive electrode layer may be unintentionally warped excessively depending on balance between stress and rigidity of the films. As a result, a gap distance between a drive electrode and a fixed electrode may vary between manufacturing lots.

The stress of each film has a distribution specific to a manufacturing process within a silicon wafer plane. Also, the stress varies between batches of a device to form the films and between manufacturing lots. According to such a stress variation, a warpage amount of the membrane and a gap (width) distance may also vary.

From this viewpoint, in the technique described in Patent Document 1, the warpage significantly changes if the stress of each film varies, leading to a large variation in gap distance. In other words, a variation between the manufacturing lots is increased.

During the drive of the cMUT element, a direct-current voltage is first applied between electrodes sandwiching a gap, thereby reducing the gap distance. Then, an alternating-current voltage is further applied to reduce and increase the gap distance, thereby generating ultrasonic waves. For this reason, if the gap distance varies among devices, applied voltages of the both direct-current voltage and the alternating-current voltage also have to be changed among the devices.

Moreover, as the magnitudes of the direct-current voltage and the alternating-current voltage, there are optimum set voltages depending on the gap distance. Therefore, when the gap varies depending on the element, the set applied voltages deviate from optimum applied voltages depending on the gap. Such a deviation of the applied voltage leads to a variation in transmitted sound pressure and also a variation in acoustic performance of generated ultrasonic waves. Thus, there may arise a problem in characteristic stability as an ultrasound probe using the cMUT element.

During reception of ultrasonic waves, in a state where the gap is reduced by application of the direct-current voltage, a change in the gap distance by vibration of the membrane is treated as a change in electrostatic capacitance and is converted into a current. Thus, charge accumulation in the element by the application of the direct-current voltage may affect the receiving sensitivity. For this reason, when there is a variation in the gap distance, received signals vary, resulting in deterioration in definition of ultrasound images. In other words, there may arise a problem in the characteristic stability as the ultrasound probe.

Moreover, in the technique described in Patent Document 2, when a beam formation position is misaligned by a variation in mask alignment in a photolithography process during device manufacturing, balance of insulating films may be impaired. As a result, warpage deformation may also vary between manufacturing lots, and the definition of ultrasound images may be deteriorated. In other words, there may arise a problem in the characteristic stability as the ultrasound probe.

The present invention is made in consideration of the above problems. It is an object of the present invention to provide an ultrasound probe with excellent characteristic stability and ultrasound equipment using the ultrasound probe.

Means for Solving the Problem

As a result of keen examination to solve the above problems, the inventors of the present invention have found out that the problems can be solved by providing a beam and forming the beam by laminating films that apply different stresses, and have completed the present invention.

Effects of the Invention

According to the present invention, an ultrasound probe with excellent characteristic stability and ultrasound equipment using the ultrasound probe can be provided.

BRIEF DESCRIPTION OF THE DRAWINGS

FIG. 6A is explanatory diagrams of a distance variation, FIG. 6A showing when there is no warpage.

FIG. 6B is explanatory diagrams of a distance variation, FIG. 6B showing when a warpage deformation amount is changed.

FIG. 6C is explanatory diagrams of a distance variation, FIG. 6C showing when a warpage deformation amount is changed.

FIG. 6D is explanatory diagrams of a distance variation, FIG. 6D showing when a warpage deformation amount is changed.

MODES FOR CARRYING OUT THE INVENTION

With reference to the drawings, a mode for carrying out the present invention (this embodiment) is described below. First, with reference to FIGS. 1 and 2, description is given of an entire configuration of an ultrasound probe according to this embodiment is described. Then, with reference to FIGS. 3 and 4, description is given of a configuration of a cMUT element applied to the ultrasound probe according to this embodiment.

<Entire Configuration of Ultrasound Probe According to this Embodiment>

Figure 1:
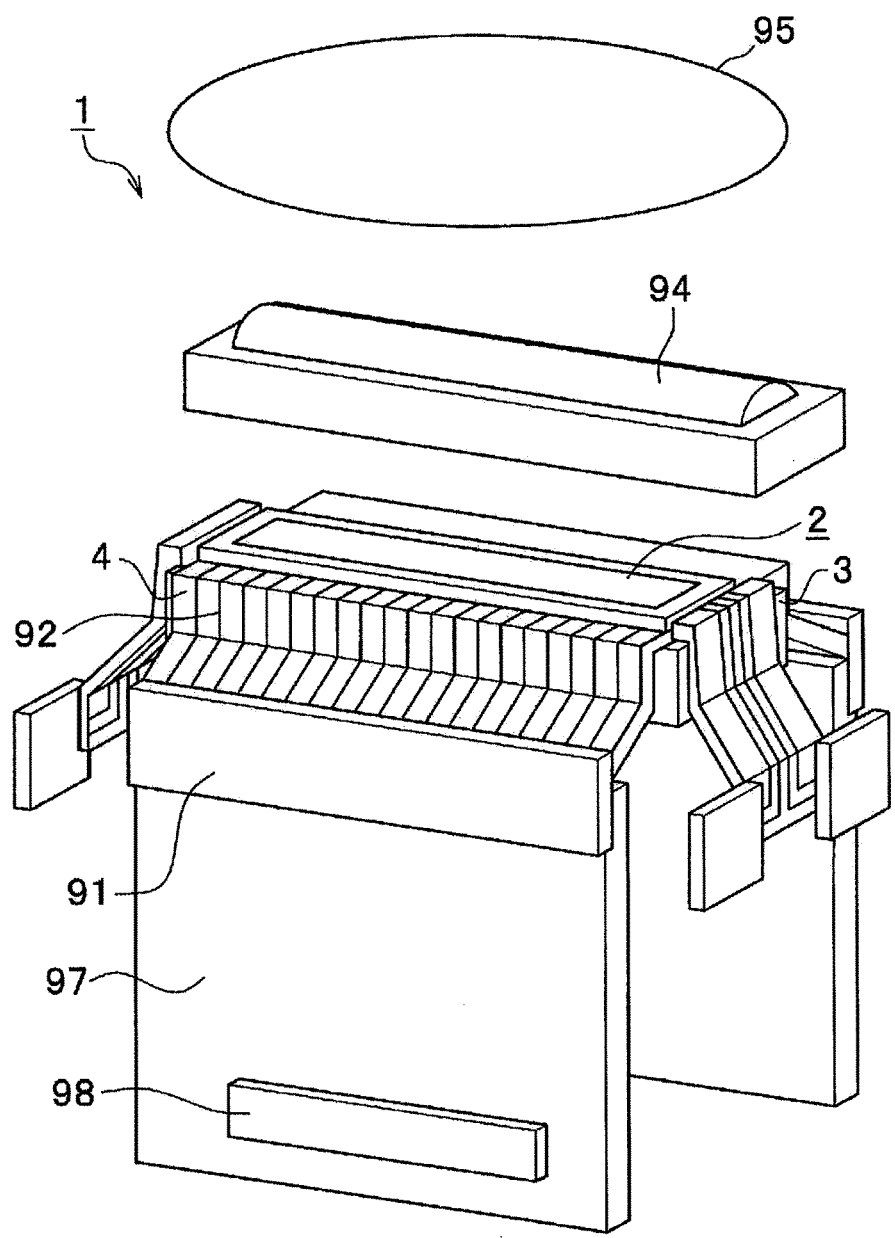
FIG. 1 is a diagram showing a schematic configuration of an ultrasound probe according to an embodiment of the present invention.

As shown in FIG. 1, an ultrasound probe 1 according to this embodiment includes a cMUT element 2, a backing 3, a flexible printed circuits 4, a connector 91, a wiring 92, a circuit board 97 and a connection terminal 98. The ultrasound probe 1 is used for human body examinations (examination of circulatory organs such as a heart and blood vessels, abdominal examination, and the like) in a medical institution, for example.

The ultrasound probe 1 includes the cMUT element 2 at a tip of the backing 3. The cMUT element 2 irradiates a subject 95 with ultrasonic waves through an acoustic lens 94 to be described later, and receives the ultrasonic waves reflected from the subject 95. Details on this point are described later. The cMUT element 2 is connected by wire bonding to the flexible printed circuits 4 having the wiring 92 connected to the connector 91. The connector 91 is connected to the circuit board 97 (no specific circuits are shown). The connection terminal 98 on the circuit board 97 is connected to ultrasound equipment 201 (see FIG. 7).

The ultrasound equipment 201 (to be described in detail later) drives the cMUT element 2 by sending an electrical signal thereto, and performs imaging of a signal formed by the ultrasonic waves received from the subject 95. On a surface of the cMUT element 2, the acoustic lens 94 made of silicon resin is provided to focus the ultrasonic waves generated from the cMUT element 2 toward the subject. The cMUT element 2 transmits and receives the ultrasonic waves to and from the subject 95 such as a human body through the acoustic lens 94.

Figure 2:
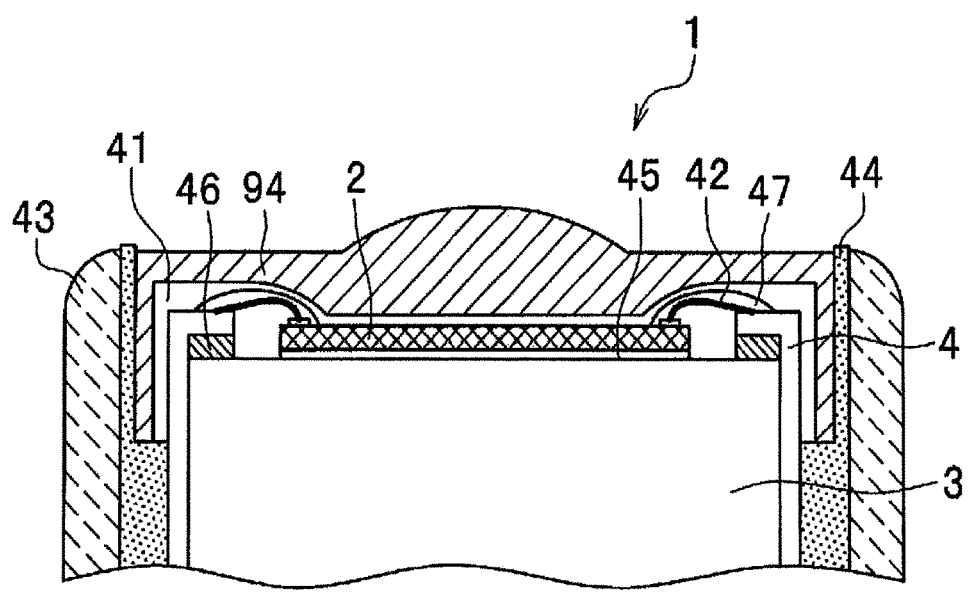
FIG. 2 is a cross-sectional view near a cMUT element.

Next, with reference to FIG. 2, a configuration near the cMUT element 2 in the ultrasound probe 1 is described in detail. As shown in FIG. 2, the cMUT element 2 is bonded and fixed on the backing 3 with a resin 45 interposed therebetween. Also, the flexible printed circuits 4 that transmits ultrasonic wave transmitted and received signals to a substrate (not shown) is fixed on the backing 3 with a resin 46 interposed therebetween.

The cMUT element 2 and the flexible printed circuits 4 are connected with a wire 42 by wire bonding. The wire 42 and the vicinity of the connection thereof are sealed with a sealing resin 47. Thus, the wire 42 can be fixed and electromigration due to application of a drive voltage can be prevented. On the structure thus obtained, the acoustic lens 94 is bonded and fixed with a resin 41. Moreover, the structure is housed in a case 43. A space between the case 43 and the acoustic lens 2 is filled with a resin 44.

<Configuration of cMUT Element 2>

Figure 3:
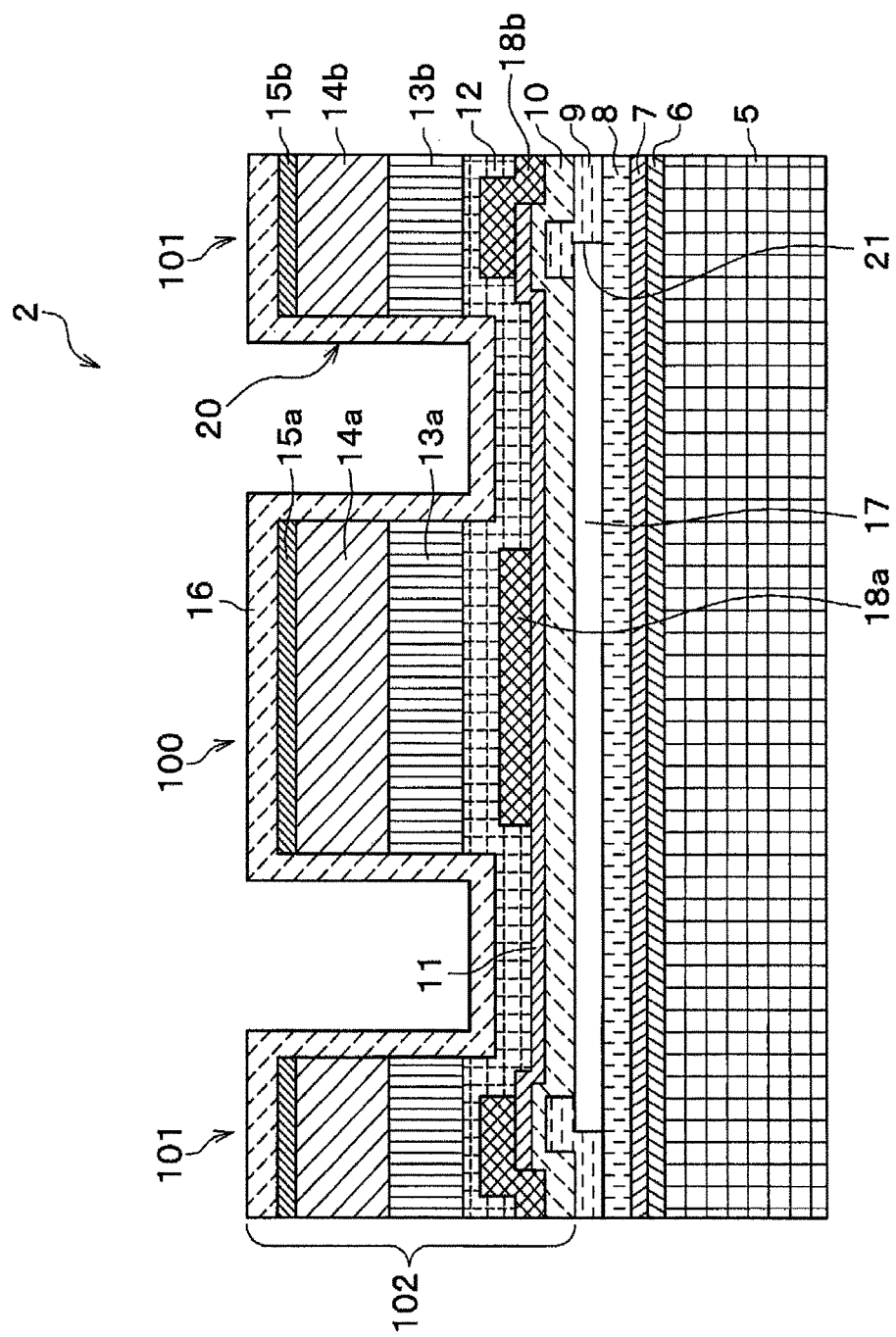
FIG. 3 is a diagram showing a membrane in the cMUT element.

FIG. 3 is an enlarged view of the surface (surface facing the acoustic lens 94) of the cMUT element 2 applied to the ultrasound probe 1. Note that the cMUT element 2 normally includes multiple cells. FIG. 3 shows an enlarged view of one of the multiple cells.

The cMUT element 2 includes a silicon substrate 5, a lower electrode 7, an upper electrode 11 and insulating films 6, 8, 9, 10, 12, 13a, 13b, 14a, 14b, 15a, 15b, 16, 18a and 18b. Also, a cavity 17 is formed between the insulating films 8 and 10.

The insulating films and the electrodes are laminated on the surface of the silicon substrate 5. To be more specific, the insulating film 6, the lower electrode 7, the insulating film 8, the insulating film 9, the insulating film 10, the upper electrode 11, the insulating films 18a and 18b and the insulating film 12 are laminated in this order on the silicon substrate. Also, the cavity 17 is provided between the insulating films 8 and 10. Moreover, on a surface of the insulating film 12, a beam part 100 and two rim parts 101 are provided.

A membrane 102 is an assembly of the insulating films, the electrodes and the cavity 17 provided on the silicon substrate. Ultrasonic waves are generated by vibration of the membrane 102 during application of an alternating-current voltage. The membrane 102 includes the beam part 100 and the rim parts 101.

The beam part 100 is provided on an upper surface of the insulating film 18a near the center of the upper electrode 11. In the beam part 100, the insulating films 12, 13a, 14a and 15a are laminated in this order from the silicon substrate 5 side. More specifically, as shown in FIG. 3, the insulating film 16 (film that applies tensile stress) is formed on the outer surface of the cMUT element (ultrasonic transmitting and receiving element) 2. The beam part 100 is formed by laminating the insulating film 12 (film that applies tensile stress), the insulating film 13a (film that applies compressive stress), the insulating film 14a (film that applies tensile stress) and the insulating film 15a (film that applies compressive stress) are laminated in this order on the silicon substrate (substrate) 5. An upper surface and side surfaces of the beam part 100 are covered with the insulating film 16. The number of layers (the number of laminated films) included in the beam part 100 is larger than the number of layers in the membrane 102 between the beam part 100 and the rim part 101 (i.e., at the bottom of a recess part formed between the beam part 100 and the rim part 101).

The rim parts 101 are provided on an upper surface of the insulating film 18b so as to partially overlap with both ends of the upper electrode 11. More specifically, as shown in FIG. 3, the rim parts 101 are provided distant from the beam part 100, and the rim parts 101 have a multilayer structure formed by laminating the insulating films 12, 13b, 14b and 15b (films made of materials different in stress). Each of the rim parts 101 protrudes toward the cavity 17 from a cavity edge 21 (edge of the cavity 17). The strength of the cMUT element 2 can be improved by providing the rim parts 101. Moreover, high rigidity of the rim parts 101 enables more favorable vibration of the membrane 102.

The rim parts 101 and 101 are provided such that the both ends (ends in a horizontal direction of the page space) of the upper electrode 11 are formed below the rim parts 101 and 101 shown in FIG. 3. Each of the rim parts 101 includes the insulating films 12, 13b, 14b and 15b as constituent elements, which are laminated in this order from the silicon substrate 5 side. Also, an upper surface of the rim part 101 and a surface thereof facing the beam part 100 are covered with the insulating film 16. As in the case of the beam part 100, the number of layers included in the rim part 101 is larger than the number of layers in the membrane 102 between the beam part 100 and the rim part 101 (i.e., at the bottom of the recess part formed between the beam part 100 and the rim part 101).

A rim edge 20 that is an edge of the rim part 101 protrudes more than the cavity edge 21 that is the edge of the cavity 17. Thus, rigidity of a portion, of the membrane 102, prone to deformation near the cavity edge 21 can be increased. Thus, warpage of the membrane 102 due to a stress variation in each of the films and a gap variation in the cavity 17 can be reduced.

Between the rim part 101 and the insulating film 8, the respective insulating films are intricately laminated. Such a laminated structure can prevent breakdown due to a leak current.

The lower electrode 7 and the upper electrode 11 are both parallel plate electrodes. The membrane 102 is warped by application of a direct-current voltage or an alternating-current voltage to the electrodes by connecting an unillustrated power source thereto. In other words, the upper electrode 11 is pulled closer to the lower electrode 7. Note that the membrane 102 is where warpage occurs due to application of the direct-current voltage to the lower electrode 7 and the upper electrode 11. Meanwhile, during application of the alternating-current voltage, the membrane 102 is where vibration occurs.

Here, the insulating films included in the cMUT element 2 are described. The insulating films included in the cMUT element 2 are made of silicon dioxide (silicon dioxide; $SiO_2$) and silicon nitride (silicon nitride; $Si_3N_4$). Specifically, the insulating films 6, 8, 9, 10, 13a, 13b, 15a, 15b, 18a and 18b (first insulating films) are made of silicon dioxide. Meanwhile, the insulating films 12, 14a, 14b and 16 (second insulating films) are made of silicon nitride. As described above, the insulating films applied to the cMUT element 2 are made of two different kinds of insulating materials. These insulating films can be formed by chemical vapor deposition or sputtering, for example.

The films made of silicon dioxide (the first insulating films) are films that apply compressive stress (compressive stress films). On the other hand, the films made of silicon nitride (the second insulating films) are films that apply tensile stress (tensile stress films). In other words, the films that apply tensile stress are made of silicon nitride, while the films that apply compressive stress are made of silicon dioxide. More specifically, in the beam part 100, the surface thereof is covered with the film made of silicon nitride, and the compressive stress film made of silicon dioxide (the insulating film 15a), the tensile stress film made of silicon nitride (the insulating film 14a), the compressive stress film made of silicon dioxide (the insulating film 13a) and the tensile stress film made of silicon nitride (the insulating film 12) are laminated in this order from the surface side. In the rim part 101, the films are also laminated approximately in the same manner.

More specifically, the ultrasound probe 1 has the cMUT element (ultrasonic transmitting and receiving element) 2 including: the silicon substrate (substrate) 5; the insulating films 6, 8, 9, 10, 12, 18a and 18b formed on the silicon substrate 5; the cavity 17 formed between the silicon substrate 5 and the insulating films 6, 8, 9, 10, 12, 18a and 18b; and the upper electrode 11 and the lower electrode 7 (a pair of electrodes) disposed parallel to the silicon substrate 5 so as to sandwich the cavity 17 (see FIGS. 1 and 3). In the ultrasound probe 1, the ultrasonic transmitting and receiving element 2 includes the beam part 100 having the multilayer structure formed by laminating the films 12, 13a, 14a and 15a made of materials different in stress on the upper electrode 11 (electrode) distant from the silicon substrate 5 among the upper electrode 11 and the lower electrode 7, as shown in FIG. 3. The beam part 100 is formed by laminating the insulating films 12 and 14a (the films that apply tensile stress) and the insulating films 13a and 15a (the films that apply compressive stress).

If the beam part is formed of only one kind of layer rather than laminating the compressive stress films and the tensile stress films, a warpage variation is likely to occur. Particularly, when a manufacturing variation among lots leads to a variation in stress among manufacturing lots, the provision of the beam part complicates the action of stress. For this reason, it is difficult to suppress a variation in membrane drive. However, when the number of layers laminated (the number of layers) is two, the variation described above can be suppressed, although a stress variation may be reflected in a warpage amount as in the case of bimetal, for example. Thus, excellent characteristic stability can be achieved. Furthermore, when the number of layers is three or more, such a variation can be more surely suppressed.

For this reason, in the ultrasound probe 1, the number of layers of the insulating films 12, 13a, 14a and 15a (films) included in the beam part 100 is larger than the number of layers of the insulating films 12 and 16 included in a part other than the beam part 100, as shown in FIG. 3. To be more specific, in the ultrasound probe 1, the beam part 100 includes four layers, while the insulating films included in the part other than the beam part 100 are two layers. As described above, the number of layers in the beam part 100 is larger than the number of layers of the insulating films included in the part other than the beam part 100. Moreover, in the ultrasound probe 1, the films that apply tensile stress (the insulating films 12 and 14a) and the films that apply compressive stress (the insulating films 13a and 15a) are insulating films.

In the beam part 100, the films that apply compressive stress and the films that apply tensile stress are laminated. Accordingly, even if stresses of the respective insulating films vary due to a variation, such a laminated structure of the beam part 100 achieves a balance between the tensile stress films and the compressive stress films. As a result, a variation in warpage of the membrane 102 among the manufacturing lots can be reduced, and a variation in gap distance of the cavity 17 can be reduced.

Moreover, buckling occurs when the sum of the stresses of the respective insulating films included in the membrane 102 is compressive stress. This may lead to a situation where the membrane 102 no longer vibrates normally or where cracks are caused by buckling in some cases. Accordingly, it is preferable that the sum of the stresses of the respective insulating films is tensile stress. Specifically, the sum of the stresses of the insulating films (films) 6, 8, 9, 10, 12, 18a and 18b formed on the silicon substrate (substrate) 5 is the tensile stress. Furthermore, it is preferable that the average of the stresses of the respective insulating films is also the tensile stress. For this reason, the number of layers in the cMUT element 2 is determined such that the sum of the stresses of the respective insulating films is the tensile stress.

Note that the insulating film 16 covering the beam part 100 and the rim parts 101 is the film that applies the tensile stress as described above, and also has a function to protect the surface of the cMUT element 2 (e.g., from mixing of foreign substances, moisture and the like).

Figure 4:
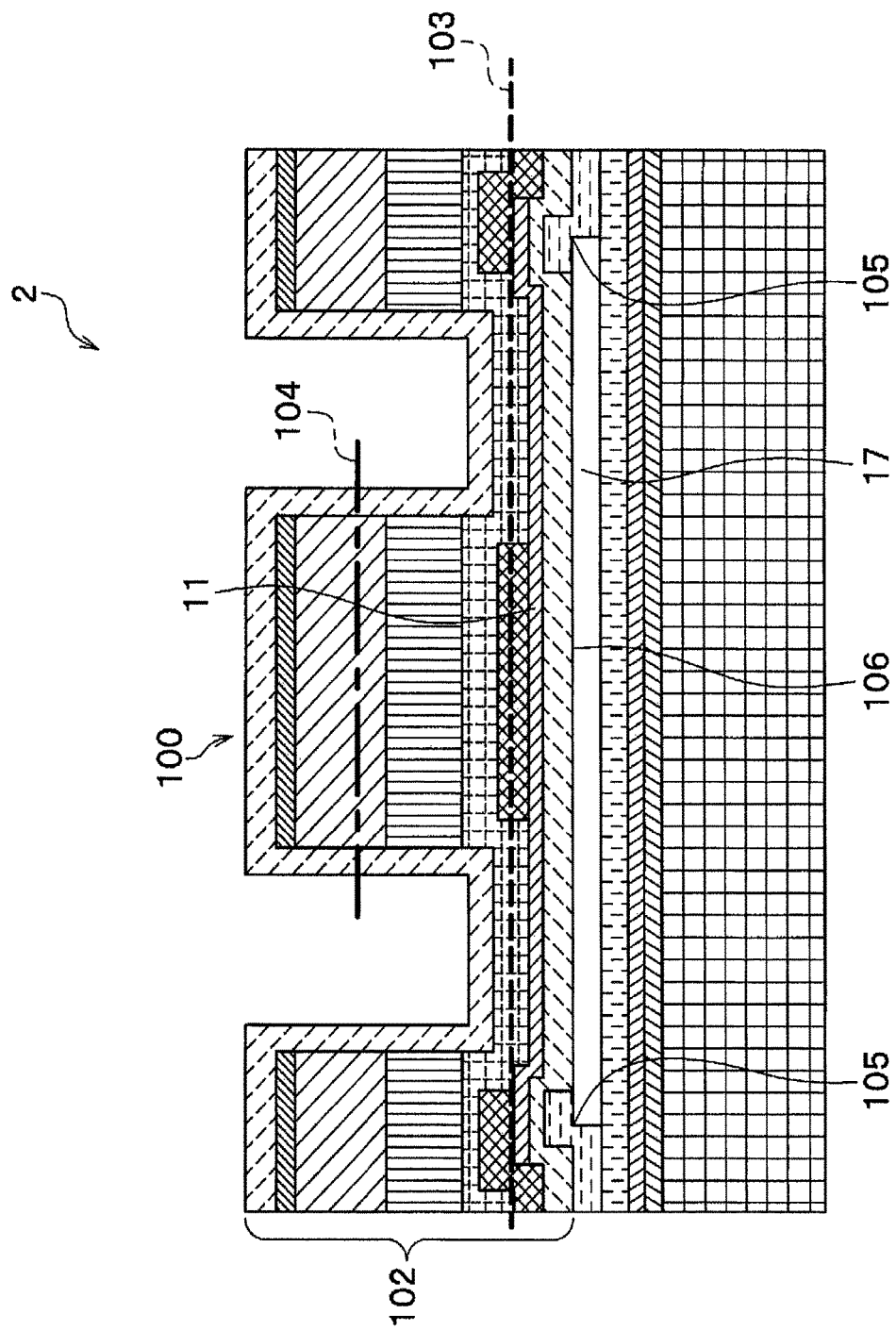
FIG. 4 is an explanatory diagram of a stress neutral surface of the membrane and a beam neutral surface of a beam part.

Next, with reference to FIG. 4, description is given of a relationship between a thickness of the membrane 102 and a height of the beam part 100. In the cMUT element 2, as shown in FIG. 4, a stress neutral surface 103 of the membrane 102 is positioned lower than a beam neutral surface 104 of the beam part 100. More specifically, when comparing the stress neutral surface 103 and the beam neutral surface 104, the stress neutral surface 103 is set closer to the upper electrode 11. Accordingly, heights of the membrane 102 and the beam part 100 are set such that the stress neutral surface 103 and the beam neutral surface 104 satisfy such a relationship.

Specifically, in the ultrasound probe 1, as shown in FIG. 4, the stress neutral surface 103 of the insulating films 6, 8, 9, 10, 12, 18a and 18b formed on the silicon substrate (substrate) 5 in a direction perpendicular to the silicon substrate 5 is located at a position closer to the silicon substrate 5 than the beam neutral surface 104 of the beam part 100 in the direction perpendicular to the silicon substrate 5 is.

Note that the "neutral surface" described above is defined as follows in this example. Specifically, when the stresses of the respective films cause bending deformation (warpage) in the membrane 102, a concave side is contracted and a convex side is elongated. In this state, a surface at the boundary therebetween where there is no contraction or elongation, i.e., distortion is zero is called the "neutral surface".

A supporting point when the membrane 102 is driven (warped and vibrated) is an upper edge 105 of the cavity 17. Also, a vibration center when the membrane 102 is driven is the vicinity of an upper surface 106 of the cavity 17. Accordingly, a bending moment generated in the membrane 102 is increased with distance of the stress neutral surface 103 from the upper surface 106. As a result, the warpage of the membrane 102 is increased and an influence rate of a stress variation in the insulating films is also increased.

In view of this, it is preferable that the stress neutral surface 103 is set as close to the upper surface 106 as possible. In other words, in the cMUT element 2, when comparing a distance between the upper surface 106 and the stress neutral surface 103 with a distance between the upper surface 106 and the beam neutral surface 104, the former distance is set to be shorter.

<Modified Example of cMUT Element 2>

Figure 5:
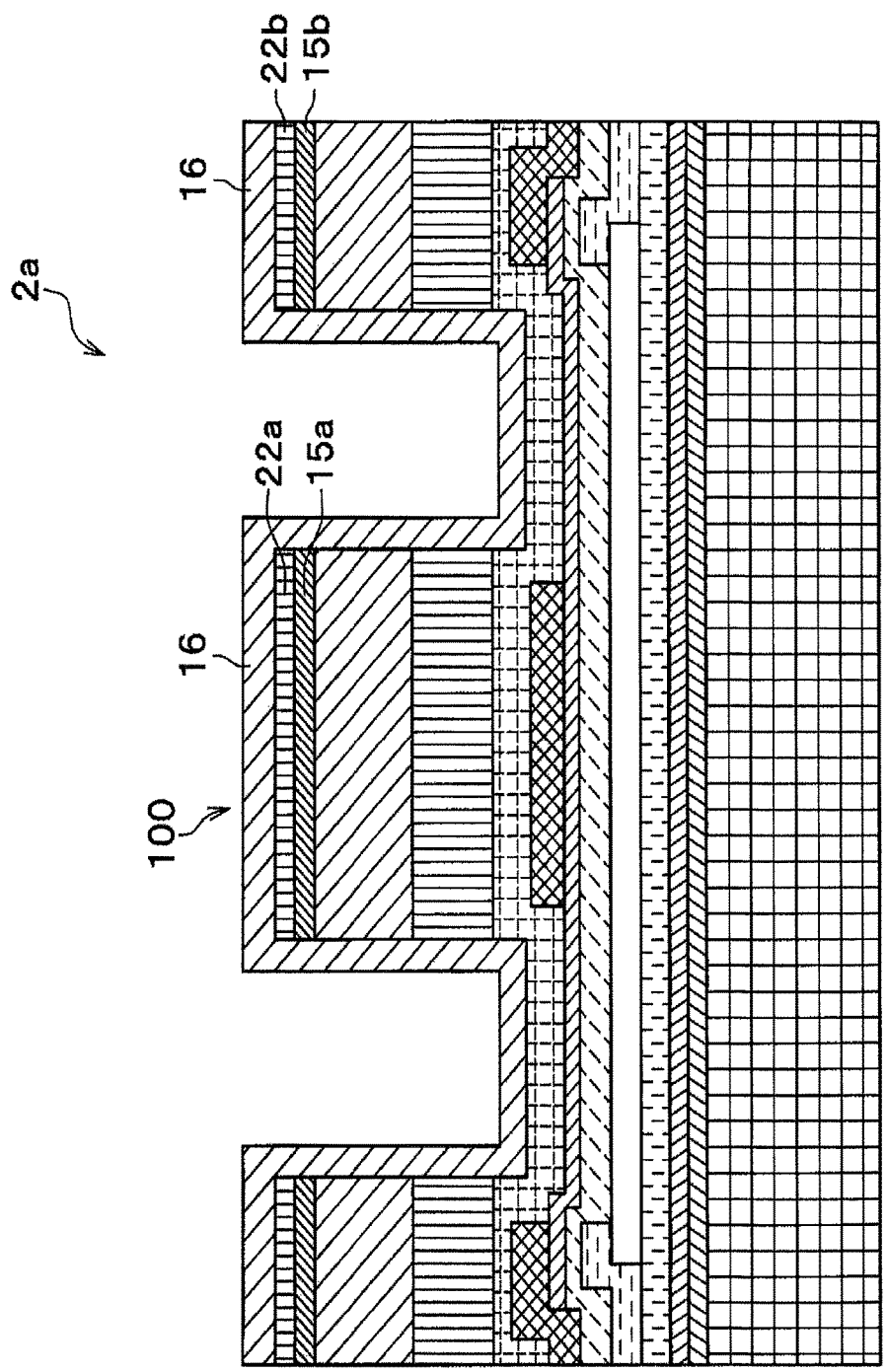
FIG. 5 is a diagram showing a membrane in another cMUT element.

FIG. 5 shows a modified example of the cMUT element 2 shown in FIG. 3. Note that, in a cMUT element 2a shown in FIG. 5, the same members as those in the cMUT element 2 shown in FIG. 3 are denoted by the same reference numerals, and detailed description thereof is omitted.

The cMUT element 2a includes a high-rigidity film 22a provided between an insulating film 15a and an insulating film 16 in a beam part 100. Also, in a rim part 101, a high-rigidity film 22b is provided between an insulating film 15b and the insulating film 16. By providing such high-rigidity films 22a and 22b, the rigidity of the membrane 102 can be increased. As a result, a warpage variation and a gap distance variation can be minimized for a stress variation in the insulating films.

Although specific materials to form the high-rigidity films 22a and 22b are not particularly limited, tungsten (W), tungsten carbide (WC), tungsten boride ($W_2B_5$), titanium nitride (TiN), titanium carbide (TiC), molybdenum (Mo), molybdenum boride ($Mo_2B_5$), molybdenum carbide ($Mo_2C$), titanium boride ($TiB_2$) and silicon carbide (SiC) are preferable. Among the above, tungsten is particularly preferable. Any one of the above may be used individually, or two or more of the above may be used in combination.

Specifically, as shown in FIG. 5, the insulating film 16 (film that applies tensile stress) is formed on an outer surface of the cMUT element (ultrasonic transmitting and receiving element) 2. Also, as the high-rigidity film 22a (uppermost film in the beam part 100), a film made of one or more selected from the group consisting of tungsten, tungsten carbide, tungsten boride, titanium nitride, titanium carbide, molybdenum, molybdenum boride, molybdenum carbide, titanium boride and silicon carbide is formed in contact with the insulating film 16 (film that applies tensile stress on the outer surface).

The following Table 1 shows Young's moduli of the materials described above. Table 1 also shows Young's moduli of silicon dioxide (the first insulating film) and silicon nitride (the second insulating film).

TABLE 1

| Material | Young's modulus (GPa) |
| --- | --- |
| Tungsten | 400 to 410 |
| Tungsten carbide | 450 to 650 |
| Tungsten boride | 770 |
| Titanium nitride | 590 |
| Titanium carbide | 470 |
| Molybdenum | 330 |
| Molybdenum boride | 670 |
| Molybdenum carbide | 540 |
| Titanium boride | 300 |
| Silicon carbide | 450 |
| Silicon dioxide | 70 |
| Silicon nitride | 140 |

As shown in Table 1, the material applicable to the high-rigidity films 22a and 22b is one having a Young's modulus larger than those of silicon dioxide and silicon nitride. Specifically, the Young's modulus of the material applicable to the high-rigidity films 22a and 22b is preferably 300 GPa or more. Moreover, such high-rigidity films 22a and 22b can further derive the effect of suppressing a variation in gap distance.

<Evaluation of Distance Variation in Membrane 102>

For the cMUT element 2 shown in FIG. 3, the cMUT element 2a shown in FIG. 5 and a cMUT element (not shown) of a comparative example, membrane distance variations are examined. Note that, in the cMUT element of the comparative example, a beam part is provided and insulating films below an uppermost film in the beam part have a two-layer structure including a silicon dioxide film and a silicon nitride film. In other words, the cMUT element of the comparative example is one including a beam part 100 and rim parts 101, from which the insulating films 12, 13a and 13b in the cMUT element 2 shown in FIG. 3 are omitted.

The distance variation is described with reference to FIGS. 6A to 6D. Note that, for simplification of illustration, FIGS. 6A to 6D shows only the members near the cavity 17 and some of the members included in the cMUT element 2 are omitted.

For the membrane, normally, an initial warpage deformation amount is determined based on stress balance among the insulating films and upper electrode film included in the membrane. When stresses of the insulating films and upper electrode vary between manufacturing lots or due to a wafer in-plane variation, the stress balance changes. Thus, the initial warpage deformation amount also changes as shown in FIGS. 6B to 6D.

Assuming that a width of the cavity 17 in its height direction is L0 in the case of initial warpage, the width of the cavity 17 in its height direction may vary as shown in FIGS. 6B to 6D due to a manufacturing lot variation or a wafer in-plane variation. For example, although the width becomes a standard width L1 in FIG. 6B, the membrane 102 is not warped much in FIG. 6C, resulting in an increased width L2 (L1<L2). On the other hand, in FIG. 6D, the membrane 102 is extremely warped, resulting in a reduced width L3 (L1>L3). Such a variation in warpage (variation in the width of the cavity 17 in its height direction) is attributable to a variation among manufacturing lots, for example.

When such a variation in width (i.e., a difference from the standard width L1) is excessively large, a problem as described above occurs. For this reason, such a variation in width is preferably minimized among the manufacturing lots. By reducing the variation in width, the behavior of the membrane when the same voltage (direct-current voltage and alternating-current voltage) is applied thereto can be set the same among all the manufacturing lots.

Figure 7:
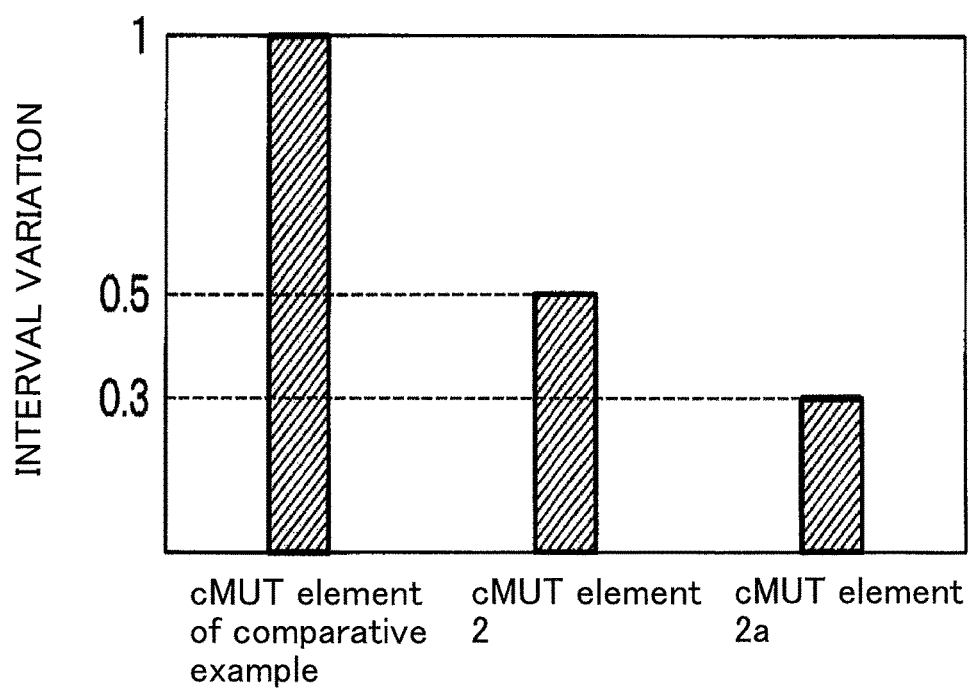
FIG. 7 is a graph showing a variation in membrane distance.

In light of the above points, the membrane distance variations (i.e., variation in width among manufacturing lots) are evaluated for the cMUT element 2, the cMUT element 2a and the conventional cMUT element. The evaluation is conducted by simulation using a finite element method. FIG. 7 shows the results.

In a graph shown in FIG. 7, a variation in width in the cMUT element when a predetermined direct-current voltage is applied thereto is evaluated a predetermined number of times, and a difference between the maximum width and the minimum width is standardized. As shown in FIG. 7, assuming that the distance variation of the cMUT element of the comparative example is 1, the distance variation of the cMUT element 2 according to this embodiment is 0.5. Also, the distance variation of the cMUT element 2a according to this embodiment is 0.3.

As described above, the use of the cMUT elements 2 and 2a according to this embodiment can reduce the distance variation. More specifically, the cMUT elements 2 and 2a according to this embodiment can reduce a variation in membrane drive. In other words, a variation in width among the manufacturing lots can be reduced. Thus, a variation in acoustic characteristics can be reduced. As a result, an ultrasound probe with excellent characteristic stability can be provided.

<Ultrasound Equipment Using Ultrasound Probe According to this Embodiment>

Figure 8A:
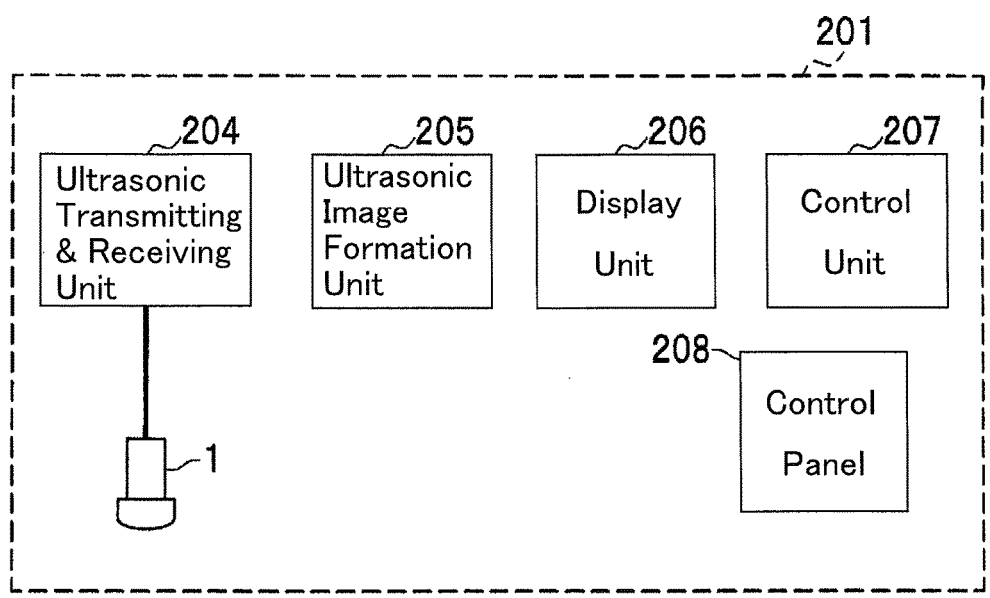
FIG. 8A is a block diagram showing a configuration of ultrasound equipment according to the embodiment.
Figure 8B:
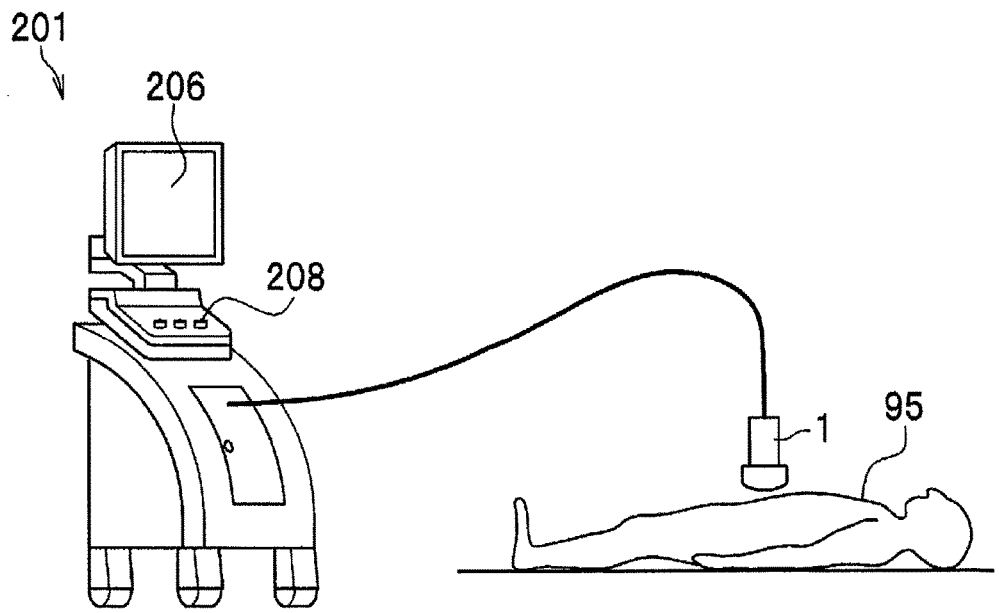
FIG. 8B is a schematic diagram thereof.

Next, ultrasound equipment using the ultrasound probe according to this embodiment (ultrasound equipment according to this embodiment) is described with reference to FIGS. 8A and 8B. FIGS. 8A and 8B are a diagram showing ultrasound equipment 201 including the ultrasound probe 1 described above.

The ultrasound equipment 201 forms and displays a two-dimensional ultrasound image, a three-dimensional ultrasound image or various doppler images of a diagnostic site by using an echo signal obtained by transmitting and receiving ultrasonic waves to and from a subject. To be more specific, as shown in FIG. 8A, the ultrasound equipment 201 includes the ultrasound probe 1, an ultrasonic transmitting and receiving unit 204 to which the ultrasound probe 1 is electrically connected, an ultrasonic image formation unit 205, a display unit 206, a control unit 207 and a control panel 208.

The ultrasound probe 1 transmits ultrasonic waves to the subject 95 and receives reflected echoes. As a cMUT element mounted on the ultrasound probe 1, the cMUT element 2 shown in FIG. 3 or the cMUT element 2a shown in FIG. 5 is applied. Since the specific configuration of the ultrasound probe 1 is described above with reference to FIG. 1 and the like, description thereof is omitted.

The ultrasonic transmitting and receiving unit 204 generates a pulsed electrical signal to generate an ultrasound signal to be transmitted to the subject 95. The ultrasonic transmitting and receiving unit 204 includes: a transmission pulse generator configured to transmit the generated electrical signal to the ultrasound probe 1; and a converter configured to convert the echo signal received by the ultrasound probe 1 into an electrical signal. The ultrasonic transmitting and receiving unit 204 is formed using any commercial ultrasonic transceiver or the like, for example.

The ultrasonic image formation unit 205 forms a two-dimensional ultrasound image, a three-dimensional ultrasound image or various doppler images from received signals. To be more specific, the ultrasonic image formation unit 205 is formed using a CPU (Central Processing Unit) or the like, for example.

The display unit 206 displays the ultrasound image formed by the ultrasonic image formation unit 205. The display unit 206 also displays information inputted by the control panel 208 to be described later, other information required for diagnosis, and the like. To be more specific, the display unit 206 is formed using an LCD (Liquid Crystal Display), a monitor device and the like, for example.

The control unit 207 controls the respective units based on control information inputted by the control panel 208 to be described later. To be more specific, the control unit 207 is formed using a CPU and the like, for example.

The control panel 208 is used by an operator to input arbitrary information so that the operator makes a desired diagnosis of the subject 95. Based on the inputted information, the control unit 207 controls the respective units. To be more specific, the control panel 208 is formed using a push button, a touch panel and the like, for example.

FIG. 8B shows specific application of the ultrasound equipment 201 to the subject 95.

In the ultrasound equipment 201 using the ultrasound probe 1, although there is a stress variation in the insulating films included in the cMUT elements 2 and 2a, each of the elements has a small variation in warpage of the membrane 102. Accordingly, a variation in the width (gap distance) of the cavity 17 is reduced. Thus, a variation in direct-current voltage to drive the cMUT elements 2 and 2a (move the membrane to the initial position) is small.

The magnitude of the direct-current voltage is a factor that determines characteristics such as transmitted sound pressure and reception sensitivity. When a variation in the direct-current voltage is reduced, a variation in transmission and reception sensitivities and a variation in signals are reduced. Accordingly, there is no display unevenness or granular rough portion in the ultrasound image displayed by the ultrasound equipment 201. Thus, the ultrasound equipment 201 can provide high-definition images.

Modified Example

Although the embodiment is described above by taking the specific embodiment as an example, the embodiment of the present invention is not limited to the above contents. For example, in the above embodiment, silicon dioxide and silicon nitride are used as the materials to form the insulating films. However, a material that applies tensile stress and a material that applies compressive stress may be used appropriately in combination.

Also, the number of layers of the insulating films included in the beam part 100 is not limited to the number of layers shown in the drawings (four layers of the insulating films 12, 13a, 14a and 15a). Any number of layers may be set, such as a single layer or multiple layers. Furthermore, the number of layers of the insulating films included in the rim part 101 is also not limited to the number of layers shown in the drawings (four layers of the insulating films 12, 13b, 14b and 15b). Any number of layers may be set, such as a single layer or multiple layers. The number of layers may differ between the beam part 100 and the rim part 101. Furthermore, in the example shown in the drawings, the number of the layers included in the beam part 100 is larger than that of the layers included in the membrane 102 between the beam part 100 and the rim part 101. However, the present invention is not limited to such a relationship of the number of layers. Also, the beam part 100 and the rim part 101 may have different heights.

Moreover, the thicknesses of the electrodes and insulating films included in the membrane 102 are also not particularly limited, but may be appropriately set. However, it is preferable that the thicknesses of the electrodes and insulating films (i.e., the heights of the membrane 102 and the beam part 100) are set so as to satisfy the relationship described with reference to FIG. 4.

Furthermore, in the example shown in the drawings, the layers that apply tensile stress and the layers that apply compressive stress are alternately laminated. However, the mode of lamination is not limited to the example shown in the drawings.

EXPLANATION OF REFERENCE NUMERALS 1 ultrasound probe
2 cMUT element (ultrasonic transmitting and receiving element)
3 backing
4 flexible printed circuits
6 insulating film
7 lower electrode (electrode)
8 insulating film
9 insulating film
10 insulating film
11 upper electrode (electrode)
12 insulating film (second insulating film)
13a, 13b insulating film (first insulating film)
14a, 14b insulating film (second insulating film)
15a, 15b insulating film (first insulating film)
16 insulating film
17 cavity
18a, 18b insulating film
20 rim edge
21 cavity edge
41 resin
42 wire
43 case
44 resin
45 resin
46 resin
47 sealing resin
91 connector
92 wiring
94 acoustic lens
95 subject
97 circuit board
98 connection terminal
100 beam part
101 rim part
102 membrane
103 stress neutral surface
104 beam neutral surface
105 upper edge
106 upper surface
201 ultrasound equipment
204 ultrasonic transmitting and receiving unit
205 ultrasonic image formation unit
206 display unit
207 control unit
208 control panel

The invention claimed is:

1. An ultrasound probe comprising:
an ultrasonic transmitting and receiving element including a substrate, an insulating film formed on the substrate, a cavity formed between the substrate and the insulating film, and a pair of electrodes disposed parallel to the substrate so as to sandwich the cavity,
wherein the ultrasonic transmitting and receiving element includes a multilayer structure formed by laminating insulating films, including a beam part, rim parts, and recess parts formed between the beam part and the rim parts, the beam part being disposed on the one electrode more distant from the substrate than the other electrode of the pair of electrodes and disposed above the cavity,
wherein the insulating films of the beam part are made of materials different in stress and include a film that applies tensile stress and a film that applies compressive stress,
wherein a number of layers of the insulating films included in the beam part is greater than a number of layers of insulating films included in the recess parts between the beam part and the rim parts, and
wherein a width of the beam part in a direction between the recess parts is less than a width of the cavity.

2. The ultrasound probe according to claim 1, wherein a stress neutral surface of the insulating film formed on the substrate in a direction perpendicular to the substrate is located at a position closer to the substrate than a beam neutral surface of the beam part in the direction perpendicular to the substrate.

3. The ultrasound probe according to claim 1, wherein a film that applies tensile stress is formed on an outer surface of the ultrasonic transmitting and receiving element, and
the beam part is formed by laminating a film that applies tensile stress, a film that applies compressive stress, a film that applies tensile stress and a film that applies compressive stress in this order from the side closest to the substrate.

4. The ultrasound probe according to claim 1, wherein the film that applies tensile stress is made of silicon nitride, and
the film that applies compressive stress is made of silicon dioxide.

5. The ultrasound probe according to claim 1, wherein a film that applies tensile stress is formed on an outer surface of the ultrasonic transmitting and receiving element, and
a film made of one or more selected from the group consisting of tungsten, tungsten carbide, tungsten boride, titanium nitride, titanium carbide, molybdenum, molybdenum boride, molybdenum carbide, titanium boride and silicon carbide is formed as an uppermost film in the beam part to be in contact with the film that applies tensile stress on the outer surface.

6. The ultrasound probe according to claim 1, wherein a sum of stresses of the films formed on the substrate is tensile stress.

7. The ultrasound probe according to claim 1, wherein the rim parts have a multilayer structure formed by laminating films made of materials different in stress, and
the rim parts overhang respective sides of the cavity at the edges of the cavity.

8. Ultrasound equipment comprising the ultrasound probe according to claim 1.

9. An ultrasound probe comprising:
an ultrasonic transmitting and receiving element including a substrate, an insulating film formed on the substrate, a cavity formed between the substrate and the insulating film, and a pair of electrodes disposed parallel to the substrate so as to sandwich the cavity,
wherein the ultrasonic transmitting and receiving element includes a beam part with a multilayer structure as a first portion, recess parts as second portions, and rim parts as third portions, the second portions being disposed between the first portion and the third portions, each of the portions being formed by laminating films,
wherein the first portion and the third portions have an equal first number of layers of insulating films, and the first number of layers of the insulating films in the first portion and the third portions is greater than a second number of layers of insulating films of the second portions,
wherein the first portion is formed by laminating a film that applies tensile stress as one of the insulating films and a film that applies compressive stress as another of the insulating films, and
wherein the first portion is disposed on the one electrode more distant from the substrate than the other electrode of the pair of electrodes and disposed above the cavity, and the third portions being disposed above respective edges of the cavity,
wherein a width of the first portion in less than a width of the cavity.

10. The ultrasound probe according to claim 9,
wherein the third portions partially overlap respective ends of the one electrode more distant from the substrate than the other electrode of the pair of electrodes.

* * * * *